United States Patent [19]
Elliott et al.

[11] Patent Number: 4,736,065
[45] Date of Patent: Apr. 5, 1988

[54] PESTICIDES

[75] Inventors: Michael Elliott, Stevenage; Norman F. Janes, Luton; David A. Pulman, Caddington; Diana M. Johnson, Harpenden, all of England

[73] Assignee: National Research Development Corporation, England

[21] Appl. No.: 908,611

[22] Filed: Sep. 17, 1986

Related U.S. Application Data

[63] Continuation of Ser. No. 670,548, Nov. 13, 1984, abandoned.

[30] Foreign Application Priority Data

Nov. 21, 1983 [GB] United Kingdom ............... 8331036
Dec. 7, 1983 [GB] United Kingdom ............... 8332630

[51] Int. Cl.$^4$ ............................................. C07C 103/22
[52] U.S. Cl. ................................. 564/180; 260/404; 564/172; 560/56; 560/100
[58] Field of Search ............... 260/404; 560/56, 100; 564/172, 180

[56] References Cited

FOREIGN PATENT DOCUMENTS 111105 6/1984 European Pat. Off.
0090077 7/1981 Japan.
0087504 7/1981 Japan.
0087505 7/1981 Japan.
0212150 12/1982 Japan.

OTHER PUBLICATIONS

Elliott et al, *Agric. Biol. Chem.*, 50(5), (1986), pp. 1347-1349.
Elliott et al, *Pestic. Sci., (1987), 18, pp. 211-221, 223-228 and 191-201.*
Pring, B. G., *Journal of the Chemical Society: Perkin Transactions I*, No. 7, Jul. 1982, pp. 1493-1498.
English Translation of Japanese Pat. Publ. (Kokai) No. 212150/1982.

Miyakado et al, Kyoto Conference Abstract, 1982.
Meisters et al, Aust. J. Chem., 19, (1966), 1215-1220.

*Primary Examiner*—Anton H. Sutto
*Assistant Examiner*—Elizabeth A. Hanley
*Attorney, Agent, or Firm*—Jacobs & Jacobs

[57] ABSTRACT

A compound of Formula I:

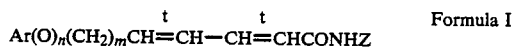

wherein:

Ar represents a polynuclear carboxyclic or heterocyclic fused ring system having at least one carbocylic or heterocyclic ring of aromatic character, the polynuclear ring system optionally carrying one or more of the substituents halogen, $C_1$-$C_6$ alkyl —$CF_3$, or —$OCF_yH_{3-y}$, wherein y is 0–3;

n is 0 or 1 and m is 1–11

Z represents a group of Formula:

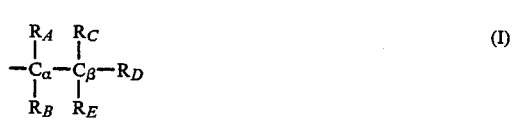

wherein:

$R_A$ and $R_B$ which may be identical or different each represent hydrogen or methyl;

$R_C$ represents methyl;

$R_D$ represents methyl, ethyl, n-propyl, isopropyl, t-butyl, or vinyl; and $R_E$ represents hydrogen or methyl or wherein:

$R_C$ and $R_D$ together with $C_\beta$ form a cyclopropane or a cyclobutane ring or goether form a methylene group (=$CH_2$) or wherein:

$R_A$ and $R_B$ together with $C_\alpha$ and $C_\beta$ form a cyclobutane ring.

20 Claims, No Drawings

PESTICIDES

CROSS-REFERENCE

This is a continuation of Ser. No. 670,548 filed Nov. 13, 1984 now abandoned.

This invention relates to pesticidal compounds, compositions, the application and production thereof and in particular to pesticidal amides.

Accordingly, the present invention comprises a compound of Formula I.

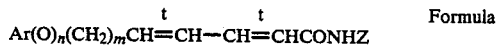

Formula I wherein

Ar represents a polynuclear carboxylic or heterocyclic fused ring system having at least one carbocylic or heterocyclic ring of aromatic character, the polynuclear ring system optionally carrying one or more of the substituents halogen, $C_1$–$C_6$ alkyl, —$CF_3$, or —$OCF_yH_{3-y}$, wherein y is 0–3;
n is 0 or 1 and m is 1–11
Z represents a group of Formula:

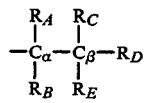

(Ia)

wherein:

$R_A$ and $R_B$ which may be identical or different each represent hydrogen or methyl;

$R_C$ represents methyl;

$R_D$ represents methyl, ethyl, n-propyl, isopropyl, t-butyl, or vinyl; and $R_E$ represents hydrogen or methyl or wherein:

$R_C$ and $R_D$ together with $C_\beta$ form a cyclopropane or a cyclobutane ring or toether form a methylene group (=$CH_2$) or wherein:

$R_A$ and $R_B$ together with $C_\alpha$ and $C_\beta$ form a cyclobutane ring.

The ring attached to oxygen or carbon respectively of $(O)_n$ or $(CH_2)_m$ in the chain is typically aromatic and preferably benzenoid.

In preferred embodiments according to the present invention Ar is of Formula II.

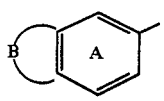

(II)

wherein B represents a 5 or 6 membered carbocyclic or heterocyclic ring optionally fused to a further such ring C. Ar may contain only two rings as for example when Ar represents naphthyl or ring B may be fused to a further ring C in which case when ring B is 5-membered the ring system may be linear as for example in fluorenyl or dibenzofuranyl. When, however, ring B is 6-membered, for example A and B together represent naphthyl, any further ring C is usually fused to ring B across the 5, 6 or 7, 8 positions so that the ring system is non-linear as for example in phenanthrenyl.

At least when Ar comprises a naphthyl ring system it is preferably substituted by one or more halogen atoms (usually chlorine, bromine or fluorine) which may be identical or different, substitution in ring B for example at the 5, 6 and 7 positions, being of particular interest. Usually mono- or disubstitution is preferred and the 5-bromo 2-naphthyl moiety is especially preferred.

Although n may be 0 or 1 and m 1–11, when n is 0, m is preferably 1 or 7–9 and especially 8 and when n is 1, m is preferably 6–8 and especially 7.

In the group Z, it is generally preferably for $R_A$ and $R_B$ to both represent hydrogen or for one of $R_A$ and $R_B$ to represent hydrogen and the other to represent methyl. $R_C$ preferably represents methyl, $R_D$ methyl or vinyl, and $R_E$ hydrogen or methyl, the groups —$CH_2CHMe_2$, —$CH_2CMe_3$, —$CH_2CHMeEt$—$CH$-$MeCHMe_2$ and —$CH_2CMe_2CH$=$CH_2$ being of especial interest.

In accordance with a further aspect of the present invention, a pesticidal composition comprises a compound of Formula I incorporated in an emulsion, emulsifiable concentrate, spray, aerosol, wettable powder, mosquito coil or vapour mat or is carried by a dust or dry granular solid.

It will be appreciated that compositions of the present invention can be prepared, for example, by mixing one or more compounds of Formula I with an appropriate solid carrier, solvent or diluent which may contain a surface active agent. The compositions may also contain synergists, or pesticidally active compounds, for example synthetic pyrethroids, to improve kill or knock-down or both.

Pesticidal compositions according to the present invention normally contain from 0.001 to 25% by weight of the compound of Formula I but the compositions can contain higher concentrations of active ingredient of Formula I e.g. up to 95% for compositions to be sold as concentrates for dilution before use by the ultimate user.

The compositions of the invention may include diluents such as hydrocarbon oils, e.g. xylene or other petroleum fractions, water, anionic, cationic, or non-ionic surface-active agents, anti-oxidants and other stabilisers as well as perfumes and colouring matters. These inert ingredients may be of the type and in proportions such as are conventionally used in pesticidal compositions.

Compositions according to the present invention and compounds of Formula I find application as insecticides for controlling weevils and aphids, for example, and are also of interest for the control of acarids (acarine species), e.g. mites and ticks.

Accordingly, in a further aspect, the present invention comprises a method of pest control in which a pest or an environment which is susceptible to attack by pests is treated with a pesticidal compound of Formula I or a pesticidal composition as hereinbefore described. Control may be exerted in a domestic or agricultural scale.

Compounds of Formula I may be produced by a Wittig reaction.

According to a further aspect of the present invention, a process for the production of a compound of Formula I comprises treating a phosphorane of Formula III

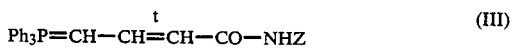

(III)

with a carbonyl compound of Formula IV:

(IV)

in which Formulae Ar, Z, n and m are as hereinbefore defined.

Aldehydes of Formula IV are preparable by the following routes or adaptations thereof. (All temperatures mentioned in this specification are in 0° C.).

ROUTE A

(a) 5-Bromo-2-hydroxymethyl-naphthalene

Methyl 5-bromo-2-naphthoate (6.0 g) in benzene (100 ml) was cooled at 7° and a 70% solution of Vitride (sodium dihydro bis-2-methoxyethoxy aluminate) (10 ml) in benzene (20 ml)) was added dropwise with stirring. The solution was stirred for 4 hours at this temperature and decomposed with water and dilute hydrochloric acid. The benzene solution was separated and washed successively with dilute acid, saturated sodium bicarbonate solution and saturated sodium chloride solution, dried over sodium sulphate and evaporated to give a solid (4.8 g), m.p. 76°–77°.

The following are similarly prepared.

| | |
|---|---|
| 2-Hydroxymethyl-9,10-dihydrophenanthrene | $n_D^{20}$ 1.6530 |
| 2-Hydroxymethylphenanthrene | m.p. = 125–127° |
| 5,8-Dibromo-2-hydroxymethylnaphthalene | m.p. = 88–90° |
| 9-Bromo-3-hydroxymethylphenanthrene | m.p. = 136–142° |
| 6-Bromo-2-hydroxymethylnaphthalene | m.p. = 70–71° |

(b) 5-Bromo-2-naphthaldehyde

The 5-bromo-2-hydroxymethylnaphthalene alcohol (4.8 g) dissolved in methylene chloride (100 ml) was stirred at room temperature while pyridinium chlorochromate (7.6 g) was added in portions over 10 minutes. After stirring for a further 4 hours, ether (200 ml) was added and the mixture filtered through a pad of celite/charcoal. The filtrate was concentrated under reduced pressure and chromatographed on silica, eluting with ether. Evaporation yielded the aldehyde (3.8 g), m.p. 73°–74°.

The following are similarly prepared.

| | |
|---|---|
| 9,10-Dihydrophenanthrene-2-carboxaldehyde | $n_D^{20}$ 1.6804 |
| Phenanthrene-2-carboxaldehyde | m.p. = 54–55° |
| 5,8-Dibromo-2-naphthaldehyde | m.p. = 83–87° |
| 9-Bromo-3-phenanthraldehyde | m.p. = 130–32° |
| 6-Bromo-2-naphthaldehyde | m.p. = 50–52° |

This method is of general applicability for the conversion of known esters ArCOOMe to aldehydes ArCHO.

ROUTE B₁

(a) Methyl-5-bromo-2-naphthylvinyl ether

A solution of phenyllithium (10.2 ml of a 2.7M solution in cyclohexane/ether) was added to a stirred suspension of methoxymethyltriphenylphosphonium chloride (6.4 g) in dry ether (100 ml) under nitrogen. After 30 minutes, a solution of 5-bromo-2-naphthaldehyde (2.8 g) in ether (20 ml) was added and stirring continued overnight. A few drops of water were added and the solution decanted, concentrated under reduced pressure and chromatographed on silica eluting with 50% ether/petrol. Evaporation yielded a gum (3.5 g), $n_D^{20}$ = 1.6630.

The following are similarly prepared.

| | $n_D^{20}$ |
|---|---|
| Methyl 2-phenanthrenylvinyl ether | Semi-solid |
| Methyl 9,,10-dihydrophenanthrenylvinyl ether | 1.6650 |
| Methyl 2-dibenzofuranylvinyl ether | 1.6406 |

(b) 5-Bromo-2-naphthaleneacetaldehyde

The methyl 5-bromo-2-naphthylvinyl ether (2.8 g) dissolved in tetrahydrofuran (55 ml) was stirred with concentrated hydrochloric acid (10 ml) for 1 hour at room temperature. Ether and water were added and the organic solution separated and washed with water, saturated sodium bicarbonate and saturated sodium chloride solutions. Evaporation gave a liquid (2.8 g), $n_D^{20}$ = 1.6444.

The following are similarly prepared.

| | $n_D^{20}$ |
|---|---|
| Phenanthrene-2-acetaldehyde | 1.6702 |
| 9,10-Dihydrophenanthrene-2-acetaldehyde | 1.6372 |
| Dibenzofuran-2-acetaldehyde | 1.6304 |

This method is of general applicability for the conversion of known aldehydes AfCHO to aldehydes of Formula IV: ArCH₂—CHO.

ROUTE B₂

To the solution produced by reacting sodium (0.92 g) in dry ethanol (60 ml) was added methoxymethyltriphenylphosphonium chloride (15.2 g). After stirring at room temperature for 0.5 hours, 2-naphthaldehyde (5.5 g) was added and the mixture heated at reflux for 5 hours. The mixture was evaporated to dryness and extracted with boiling ether, cooled to precipitate triphenylphosphine oxide, filtered and evaporated. The residue in dichloromethane (5 ml) was passed through a column of alumina and eluted with hexane to give 2-(2-methoxyvinyl) naphthalene (3.6 g), $n_D^{20}$ 1.6505, which was hydrolysed in dioxan (50 ml) containing 2N sulphuric acid (5 ml) at 70° for 5 hours. After adding water, the mixture was extracted with ether, and the extract washed, (saturated sodium chloride), dried, (sodium sulphate) and evaporated to give 2-naphthylacetaldehyde (3.25 g) $n_D^{20}$ 1.6232.

ROUTE C

2-Fluorenyl acetaldehyde

A solution (2 ml) of 2-bromofluorene (4.6 g) in dry tetrahydrofuran (20 ml) was added to magnesium (0.46 g) covered with tetrahydrofuran and stirred under nitrogen. Reaction was initiated using iodine and after stirring for 15 minutes the mixture was cooled to 0° when the remainder of the bromide solution was added in one portion.

A mixture of freshly distilled allyl bromide (3.0 g), dry tetrahydrofuran (30 ml) and cuprous bromide (0.3 g) was cooled in a cardice bath and stirred while the prepared Grignard solution was added. After stirring for 1 hour, at room temperature, it was decomposed wih saturated ammonium chloride solution. The mixture was extracted with ether and the ethereal solution was washed with saturated sodium chloride solution, dried over sodium sulphate and evaporated to give the crude compound (2.1 g).

The compound was dissolved in methanol/dichloromethane (50 ml) and ozonised at −20°. Dimethyl sulphide (2.0 ml) was added and the solution stirred overnight at room temperature. Water was added and the solutions separated. The organic phase was dried, evaporated and chromatographed on neutral alumina (50 g). The fractions were collected after eluting with 50% ether/petrol and yielded the ketal (0.9 g) $n_D^{20} = 1.6024$.

The ketal (0.9 g) in tetrahydrofuran (30 ml) was treated with concentrated hydrochloric acid (6. ml) and after 30 minutes water was added. The organic material was extracted into ether and washed successively with water, saturated sodium bicarbonate, saturated sodium chloride, dried over sodium sulphate and evaporated to give the acetaldehyde (0.7 g), $n_D^{20} = 1.6414$.

Table I summarises the route by which various carbonyl compounds of Formula IV may be prepared and gives characterising data on both the compounds of Formula IV and intermediate ethers of Formula Ar—CH=CHOMe.

TABLE I

| | ArCH=CHOMe $n_D^{20}$ | ArCH$_2$—CHO $n_D^{20}$ | Route |
|---|---|---|---|
| 6-bromo-2-naphthyl | 1.6510 | 1.6215 | B1 |
| 5,8-dibromo-2-naphthyl | 1.6512 | 1.6350 | B1 |
| 9-bromo-3-phenanthrenyl | 1.6678 | 1.6678 | B1 |
| 6-chloro-2-naphthyl | (Semi-solid) | (Semi-solid) | B1 |

It may be desirable to produce aldehydes from which compounds of Formula I in which n=0 and m=3-10 can be prepared by the following Route D:

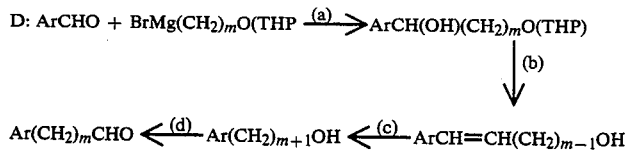

In Route D, which is applicable, for example, to compounds in which m=3, and especially substituted naphthyl compounds (a) represents treatment of the product of reaction between the Grignard reagent and aldehyde with a mild acidifying agent e.g. ammonium chloride such that the tetrahydropyranyl group (THP) is retained. The step (b) represents treatment with a dehydrating agent such a phosphorus pentoxide, (c) hydrogenation, suitably catalysed and (d) oxidation, for example with pyridinium chlorochromate.

Aldehydes in which n=1 and m is typically 6-8 may be produced if desired by following Route E which is particularly applicable to naphthoxy compounds.

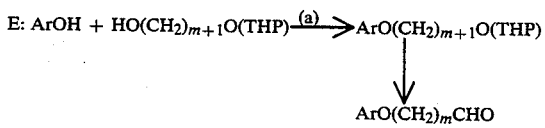

In Route (E (a) represents reaction in the presence of N,N′-dicyclohexylcarbodiimide (DCC) and (b) acidification to produce an alcohol followed by oxidation to the aldehyde using for example pyridinium chlorochromate.

The following procedure illustrates the use of Route E:

8-(2-naphthyloxy octanol, tetrahydropyranyl derivative

A mixture of 8-(2′-tetrahydropyranyloxy)-octanol (2.35 g), N,N′-dicyclohexyl-carbodiimide (2.5 g) and 2-naphthol (1.6 g) is stirred and heated at 100° C. for 20 hours. After cooling, water and chloroform are added and the mixture separated. The organic solution is washed with dilute hydrochloric acid, saturated sodium hydrogencarbonate solution, dried over sodium sulphate and evaporated to yield the product (3.0 g), $n_D = 1.5370$.

8-(2-naphthyloxy)-octanal

A mixture of the above derivative (3.0 g) in methanol (50 ml) is stirred at 50° C. with amberlyst 15 (2.0 g) for 2 hours. Filtration followed by evaporation of the filtrate yields the crude alcohol which is dissolved in dichloromethane (150 ml) and stirred at room temperature with pyridinimum chlorochromate (4.0 g) for 3 hours. Ether (200 ml) is added and the mixture filtered through a pads of cellite/charcoal, evaporated and chromatographed on silica eluting with ether. Evaporation yields the title compound (1.4 g), $n_D = 1.5148$.

The phosphorane of Formula III may be conveniently generated by treating the corresponding phosphonium salt of Formula V:

in which Formula Hal represents halogen, typically bromide, with a suitable base such as sodium ethoxide. The carbonyl compound of Formula IV may then be added to the reaction mixture and the product of Formula I isolated.

The present invention also includes within its scope of phosphonium salt of Formula V where Z and Hal$^-$ are as hereinbefore defined, provided that Z is other than an isobutyl group.

The phosphonium salt of Formula V may be produced by treatment of an amide of Formula VI.

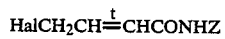

with triphenyl phosphine, the amide VI being preferably generated by reaction of the corresponding acid or a derivative thereof with amine of Formula NH$_2$Z.

In a further aspect of the present invention includes within its scope amides of Formula VI wherein Hal and Z are as hereinbefore defined, provided that Z is other than isobutyl.

In some cases compounds of Formula I may be prepared by an alternative route (the Horner-Wittig route) with advantage in that the yield may be improved and-/or the procedure simplified because of ease of product isolation. In particular the route generally gives rise to less cis product and the required product is typically isolated by simple column chromatography (e.g. on silica gel) followed by crystallisation from a suitable solvent.

According to this further aspect of the present invention, a process for the production of a compound of Formula I comprises treating a phosphonate of Formula VII.

$$(AlkO)_2P(O).CH_2CH\overset{t}{=}CH-CO-NHZ \quad (VII)$$

wherein Alk represents a lower alkyl group (say of 1 to 4 carbon atoms) and Z is as previously defined, with a base and reacting the product with a carbonyl compound of Formula IV. The base is suitably butyl lithium, sodium hydride or a sodium alkoxide e.g. sodium ethoxide.

The present invention also includes within its scope a phosphonate of Formula VII useful as an intermediate in the production of a compound of Formula I.

Phosphonates of Formula VII may be prepared from compounds of Formula VI by treatment with a trialkyl phosphite. It may be necessary or desirable to remove the compound AlkHal, typically ethyl bromide, from the reaction mixture prior to recovery of the desired product.

Compounds of Formula I may be produced by adaptation of the Wittig reaction described particularly in Procedure 1:

PROCEDURE 1

A. N-isobutyl-4-bromocrotonamide 4-bromocrotonic acid (27.1 g), thionyl chloride (54 ml) and petroleum ether (b.r. 40°-60°, 267 ml) is mixed and refluxed for 2 hours, then evaporated first to a residue using a rotary evaporator, then distilled at 1.7 kPa (13 mm Hg). The fraction b.p. 86°-90° (24.1 g), $n_D^{20}$ 1.5386) is collected as 4-bromocrotonic acid chloride. A stirred solution of the latter compound (24 g) in dry ether (120 ml) cooled continuously to less than −5° is treated during 40 minutes with isobutylamine (21. g) in dry ether (170 ml). After warming during 2 hours to 20°, dilute hydrochloric acid is added, and the clear ether layer is washed successively with sodium bicarbonate and sodium chloride solutions, then evaporated to leave as a residue (28.3 g) N-isobutyl 4-bromocrotonamide m.p. 94°-95°.

B. N-isobutyl crotonamide-4-yl triphenyl phosphonium bromide

The above amide (10.1 g) and triphenyl phosphine (13.5 g) in benzene (100 ml) are kept at 20° for 9 days, and the precipitated solid is triturated with warm ethyl acetate to leave a pale residue (19.8 g, m.p. 202°-204°) of the required product.

C. N-isobutyl 6-phenyl hexa-2(E), 4(E)-dienoic amide

The above phosphonium bromide (3.05 g) is added under nitrogen to a stirred solution of sodium (0.14 g) in dry ethanol (18 ml) at 20°. After 15 minutes freshly distilled phenylacetaldehyde (0.7 g) is added and the mixture stirred, for 21 hours. The ethanol is removed by means of a rotary evaporator, and the residue extracted three times with ether. Evaporation of the ether gave an oil which is separated by preparative HPLC into the 3(E), 5(E), (0.12 g), the 2(E), 4(Z) and the 2(E)4(E) isomers (0.7 g total) of the required product. The (2E) . (4E) isomer has m.p. 112°-114°.

The present invention is illustrated by the following Examples:

EXAMPLES 1-13

The compounds of Formula $$BrCH_2CH\overset{t}{=}CHCONHZ$$

in Table II may be prepared by following Procedure 1A.

TABLE II $$BrCH_2CH\overset{t}{=}CHCONHZ$$

| Example | NHZ | m.p. (°C.) or refractive index ($n_D^{20}$) |
|---|---|---|
| 1 | NH.CH$_2$CMe$_3$ | 1.4980 |
| 2 | NH.CH$_2$.CHMeEt | 52–53° |
| 3 | NH.CH$_2$CHMePr$^i$ | 1.5126 |
| 4 | NH.CHMe.CHMeEt | 69° |
| 5 | NH.CH$_2$–△ | 104–107° |
| 6 | NH–☐ (cis + trans) | 1.5484 |
| 7 | NH.CH$_2$–☐ | 119° |
| 8 | NH.CH$_2$CMe$_2$.CH=CH$_2$ | 1.5334 |
| 9 | NH.CH$_2$–△ | 59–61° |
| 10 | NH.CHMe.CMe$_3$ | 94° |
| 11 | NH.CH$_2$.CMe=CH$_2$ | 56–58° |
| 12 | NH.CHMeCHMe$_2$ | 109–112° |
| 13 | NH.CMe$_2$CHMe$_2$ | 1.4750 |

EXAMPLE 14

The compound $$Br^{\ominus}P^{\oplus}Ph_3CH_2CH\overset{t}{=}CH-CONHCH_2Me_3$$

is prepared from $$BrCH_2CH\overset{t}{=}CH.CONHCH_2CMe_3$$

by following Procedure 1B, the melting point being 211°-3°.

EXAMPLES 15-28

A compound of Formula $$(EtO)_2P(O)CH_2.CH\overset{t}{=}CH.CONHZ(NHZ = -NHCH_2Me_2)$$

is made from the compound Br.CH$_2$CH=CHCONHCH$_2$CHMe$_2$ by the following procedures:

(N-isobutyl crotonoamide-4-yl) diethyl phosphonate

The product of Procedure 1A (28.3 g) is added in portions to triethyl phosphite (31.1 ml) at 100° with stirring, then the temperature is gradually raised to 150°, while ethyl bromide is distilled off. After 2 hours, the mixture is distilled, and the fraction b.p. 168°-170°/0.4 mm (25.9 g) $n_D^{20}$ 1.4754 is removed and shown by NMR to be the required product.

Compounds of Formula $$(EtO)_2P(O)CH_2.CH\overset{t}{=}CH.CONHZ$$

which can be prepared from compounds of Formula $$BrCH_2CH\overset{t}{=}CHCONHZ$$

by following the latter procedure are set out in Table III with physical constants.

TABLE III $$(EtO)_2P(O)CH_2—CH\overset{t}{=}CH.CONHZ$$

| Example | NHZ | Refractive index ($n_D^{20}$) |
|---|---|---|
| 15 | NH.CH$_2$CH$_2$CHMe$_2$ | 1.4754 |
| 16 | NH.CH$_2$CHMeEt | 1.4770 |
| 17 | NH.CH$_2$CHMePr$^i$ | 1.4815 |
| 18 | NH.CHMeCHMeEt | 1.4832 |
| 19 | NH.CH$_2$—△ | 1.4812 |
| 20 | NH—□ (cis + trans) | 1.4930 |
| 21 | NH.CH$_2$—◇ | 1.4914 |
| 22 | NH.CH$_2$—△ | 1.4830 |
| 23 | NH.CHMe.CMe$_3$ | 1.4810 |
| 24 | NH.CH$_2$CMe(=CH$_2$) | 1.4753 |
| 25 | NH.CH$_2$CMe$_2$CH=CH$_2$ | 1.4793 |
| 26 | NH.CMe$_2$CHMe$_2$ | 1.4777 |
| 27 | NH.CHMeCHMe$_2$ | 1.4754 |
| 28 | NH.CH$_2$CMe$_3$ | 1.4792 |

EXAMPLES 29-65

Compounds of Formula $$Ar(O)_n(CH_2)_mCH\overset{t}{=}CH—CH\overset{t}{=}C—CONHZ$$

which can be prepared from compounds of Formula $$(EtO)_2P(O)CH_2CH\overset{t}{=}CH.CONHZ$$

and compounds of Formula Ar(O)$_n$(CH)$_m$CHO by following Procedure 2 are set out in Table IV with physical constants and bioassay data:

PROCEDURE 2

N-isobutyl-6-phenyl hexa (2E, 4E) dienoic amide

The phosphonate of Example 15 (0.21 g) in dry benzene (2.3 ml) is treated at 20° under nitrogen with a solution of butyl lithium in hexane (0.47 ml 1.6M), then 30 minutes later with freshly distilled phenylacetaldehyde (0.08 g) in benzene (1.2 ml), and stirred for 5 hours. After neutralising with glacial acetic acid water is added, and the whole extracted with ether. Purification by simple chromatography on silica gel eluting with 1:1 etherhexane gives the required product (35% yield).

Illustrative compounds are set out in Table IV with physical constants and bioassy data.

Compounds of Formula I are bioassayed by the following method:

Acetone solutions (1 μl) of compounds are applied topically by Arnold micro-applicator to the thorax of 4-day-old adult female houseflies (HF), anaethetised with ether, or to the ventral abdomen of approximately 1-week-old adult male and female mustard beetles (MB), held by suction tube. For each concentration, and for a control, two replicates, each of 15 insects, are dosed topically and the dead counted after 24 hours (HF) or 48 hours (MB); at these times end point mortalities are approached.

The results are analysed by the method of probits, to give for each test LD$_{50}$ values and standard errors for each compound, and for the standard (bioresmethrin). Comparisons between LD$_{50}$S and compound and standard give relative potencies (bioresmethrin=100).

TABLE IV

Compounds I: ArCH$_2$—CH$\overset{t}{=}$CH—CH$\overset{t}{=}$CH CONHZ

| Example No. | Ar | —NHZ | m.p. (°C.) or $n_D^{20}$ | Relative Potency HF | Potency MB |
|---|---|---|---|---|---|
| 29 | 2-naphthyl | —NHCH$_2$CHMe$_2$ | 146-8° | 3.0 | 3.0 |
| 30 | 2-naphthyl | —NHCH$_2$CMe$_3$ | 68-69° | 2.0 | 8.0 |
| 31 | 2-fluorenyl | —NHCH$_2$CHMe$_2$ | 174-176° | 1.8 | ca 5.1 |
| 32 | 2-naphthyl | —NHCH$_2$CMe$_2$CH=CH$_2$ | 77-80° | 0.8 | 3.7 |
| 33 | 2-naphthyl | —NHCH$_2$CHMeEt | 109-110° | 0.6 | 7.6 |
| 34 | 2-phenanthrenyl | —NHCh$_2$CHMe$_2$ | 143-6° | — | 5.2 |
| 35 | 5-bromo-2-naphthyl | —NHCH$_2$CHMe$_2$ | 157° | 4.7 | 25 |
| 36 | 6-bromo-2-naphthyl | —NHCH$_2$CHMe$_2$ | 123-6° | 0.5 | 2 |
| 37 | 2-dibenzofuranyl | —NHCH$_2$CHMe$_2$ | 172° | — | 6 |
| 38 | 2-naphthyl | —NHCHMeCMe$_3$ | 125-7° | 1 | 0.5 |
| 39 | 2-naphthyl | —NHCHMeCHMe$_2$ | 174-5° | 2.8 | 0.7 |

TABLE IV-continued

Compounds I: ArCH$_2$—CH$\overset{t}{=}$CH—CH$\overset{t}{=}$CH CONHZ

| | | | | | |
|---|---|---|---|---|---|
| 40 | 2-phenanthrenyl | —NHCH$_2$CMe$_3$ | 137–8° | — | 3.3. |
| 41 | 2-phenanthrenyl | —NHCHMeCHMe$_2$ | 62° | — | 1.0 |
| 42 | 2-phenanthrenyl | —NHCH$_2$CHMeEt | 123–5° | — | 2.6 |
| 43 | 5-bromo-2-naphthyl | —NHCH$_2$CMe$_3$ | 116–9° | 6.3 | 17 |
| 44 | 5-bromo-2-naphthyl | —NHCH$_2$CHMeEt | 112–8° | 3.0 | 17 |
| 45 | 2-dibenzofuranyl | —NHCH$_2$CMe$_3$ | 114° | 1.4 | 9.0 |
| 46 | 2-dibenzofuranyl | —NHCH$_2$CMe$_2$CH=CH$_2$ | 119–20° | — | 2.4 |
| 47 | 2-phenanthrenyl | —NHCH$_2$CMe$_2$CH=CH$_2$ | 1.6158 | 0.2 | 2.7 |
| 48 | 2-dibenzofuranyl | —NHCHMeCHMe$_2$ | 172–173° | 3.0 | 7.2 |
| 49 | 2-dibenzofuranyl | —NHCH$_2$CHMeEt | 138–139° | 0.95 | 9.5 |
| 50 | 5-bromo-2-naphthyl | —NHCHMeCHMe$_2$ | 154° | 10 | 22 |
| 51 | 5-bromo-2-naphthyl | —NHCH$_2$CMe$_2$CH=CH$_2$ | 88–90° | 2.5 | 10 |
| 53 | 9-bromo-3-phenanthrenyl | —NHCH$_2$CMe$_3$ | 165–167° | N.T. | 2.7 |
| 54 | 6-chloro-2-naphthyl | —NHCH$_2$CHMe$_3$ | 134–6° | 2.4 | 57 |
| 55 | 7-bromo-2-naphthyl | —NHCH$_2$CMe$_3$ | 165° | 2.9 | 11 |
| 56 | 7-chloro-2-naphthyl | —NHCH$_2$CMe$_3$ | 143–5° | 2.4 | 14 |
| 57 | 7-chloro-2-naphthyl | —NHCH$_2$CHMe$_2$ | 158° | 1.4 | 18 |
| 58 | 7-fluro-2-naphthyl | —NHCH$_2$CMe$_3$ | 110–1° | 1.4 | 8.5 |
| 59 | 9,10-dihydrophenanthrenyl | —NHCH$_2$CMe$_2$CH=CH$_2$ | 1.6158 | — | 2.7 |
| 60 | 7-fluro-2-naphthyl | —NHCMe—CHMe$_2$ | 168° | 5.0 | 3.8 |
| 61 | 5,8-dibromo-2-naphthyl | —NHCH$_2$Me$_3$ | 115–6° | 1.4 | 1.4 |

| Example No. | Ar | n | m | Z | m.p. (°C.) or n$_D^{20}$ | Relative HF | Potency MB |
|---|---|---|---|---|---|---|---|
| 62 | 2-naphthyl | 1 | 7 | —NHCH$_2$CHMe$_2$ | 83–6° | 3 | 10 |
| 63 | 2-naphthyl | 1 | 7 | —NHCH$_2$CMe$_3$ | 1.5373 | 1 | 4 |
| 64 | 2-naphthyl | 1 | 7 | —NHCH$_2$CMeEt | 62–4° | 0.4 | 4 |
| 65 | 2-naphthyl | 1 | 7 | —NHCMeCHMe$_2$ | 88–90° | 4 | 3 |
| 66 | 2-(4-bromonaphthyl) | 1 | 7 | —NHCH$_2$CHMe$_2$ | 107–9° | 0.1 ca | 3 |
| 67 | 2-naphthyl | 0 | 8 | —NHCH$_2$CHMe$_2$ | 101–2° | — | 2.0 |

We claim:

1. A compound of Formula I:

$$Ar(O)_n(CH_2)_mCH\overset{t}{=}CH-CH\overset{t}{=}CHCONHZ \quad (I)$$

wherein:
Ar is naphthyl substituted by one or more halo moieties;
n is 0 and m is 1;
$Z_n$ is a group of Formula:

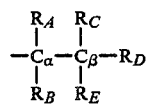

(Ia)

wherein:
R$_A$ and R$_B$ are the same or different and each is hydrogen or methyl;
R$_C$ is methyl;
R$_D$ is methyl, ethyl, n-propyl, isopropyl, t-butyl, or vinyl; and
R$_E$ is hydrogen or methyl or wherein:
R$_C$ and R$_D$ together with C$_\beta$ form a cyclopropane or a cyclobutane ring or together form a methylene group (=CH$_2$) or wherein:
R$_A$ and R$_B$ together with C$_\alpha$ and C$_\beta$ form a cyclobutane ring.

2. A compound according to claim 1, in which the naphthyl ring is substituted by one or two halo atoms.

3. A compound according to claim 2, in which the naphthyl ring is substituted at the 5, 6 or 7 positions or at any two of such positions.

4. A compound according to claim 1 in which both R$_A$ and R$_B$ are hydrogen or one of R$_A$ and R$_B$ is hydrogen and the other is methyl.

5. A compound according to claim 1, in which R$_C$ is methyl.

6. A compound according to claim 1, in which R$_D$ is methyl or vinyl.

7. A compound according to claim 1 in which R$_E$ is hydrogen or methyl.

8. A compound according to claim 1 in which Z is —CH$_2$CHMe$_2$, —CH$_2$Me$_3$, —CH$_2$MeEt, —CHMeCHMe$_2$ or —CH$_2$CMe$_2$CH=CH$_2$.

9. A pesticidal composition which comprises an effective amount of the formula I $$Ar(O)_n(CH_2)_mCH\overset{t}{=}CH-CH\overset{t}{=}CHCONHZ \quad (I)$$

wherein:
Ar is naphthyl substituted by one or more halo moieties;
n is 0 and m is 1;
$Z_n$ is a group of Formula:

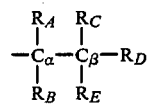

(Ia)

wherein:
R$_A$ and R$_B$ are the same or different and each is hydrogen or methyl;
R$_C$ is methyl;
R$_D$ is methyl, ethyl, n-propyl, isopropyl, t-butyl, or vinyl; and
R$_E$ is hydrogen or methyl or wherein:
R$_C$ and R$_D$ together with C$_\beta$ form a cyclopropane or a cyclobutane ring or together form a methylene group (=CH$_2$) or wherein:
R$_A$ and R$_B$ together with C$_\alpha$ and C$_\beta$ form a cyclobutane ring, in combination with a suitable diluent or carrier.

10. A composition according to claim 9 in which the naphthyl ring is substituted by one or two halo atoms.

11. A composition according to claim 10 in which the naphthyl ring is substituted at the 5, 6 or 7 positions or at any two of such positions.

12. A composition according to claim 9 in which both $R_A$ and $R_B$ are hydrogen or one of $R_A$ and $R_B$ is hydrogen and the other is methyl.

13. A composition according to claim 9 in which $R_C$ is methyl.

14. A composition according to claim 9 in which $R_D$ is methyl or vinyl.

15. A composition according to claim 9 in which $R_E$ is hydrogen or methyl.

16. A composition according to claim 9 in which Z is —CH$_2$CHMe$_2$, —CH$_2$Me$_3$, —CH$_2$MeEt, —CHMeCHMe$_2$ or —CH$_2$CMe$_2$CH=CH$_2$.

17. A compound according to claim 7, wherein said halo is bromo.

18. A compound according to claim 3, wherein said halo is bromo.

19. A composition according to claim 10, wherein said halo is bromo.

20. A composition according to claim 11, wherein said halo is bromo.

* * * * *